United States Patent [19]

Arai et al.

[11] 4,370,266
[45] * Jan. 25, 1983

[54] MYCOPLANECIN DERIVATIVES AND THEIR PREPARATION

[75] Inventors: Mamoru Arai; Tatsuo Haneishi; Mutsuo Nakajima; Akio Torikata; Ryuzo Enokita, all of Tokyo, Japan

[73] Assignee: Sankyo Company, Limited, Tokyo, Japan

[*] Notice: The portion of the term of this patent subsequent to Jun. 22, 1999, has been disclaimed.

[21] Appl. No.: 250,709

[22] Filed: Apr. 3, 1981

[30] Foreign Application Priority Data

Apr. 7, 1980 [JP] Japan .................................. 55-45402
Apr. 8, 1980 [JP] Japan .................................. 55-46003

[51] Int. Cl.³ ............................................ C07C 103/52
[52] U.S. Cl. ............................................. 260/112.5 R
[58] Field of Search .................. 260/112.5 R; 424/121

[56] References Cited

U.S. PATENT DOCUMENTS 3,365,362  1/1968  Maney et al. ...................... 424/121
3,719,656  3/1973  Jolles .............................. 260/112.5
4,108,985  8/1978  Rüegger et al. ............. 260/112.5 R
4,123,521  10/1978 Hanka et al. ...................... 424/121

Primary Examiner—Delbert R. Phillips
Attorney, Agent, or Firm—Frishauf, Holtz, Goodman & Woodward

[57] ABSTRACT

Mycoplanecin derivatives of formula (I):

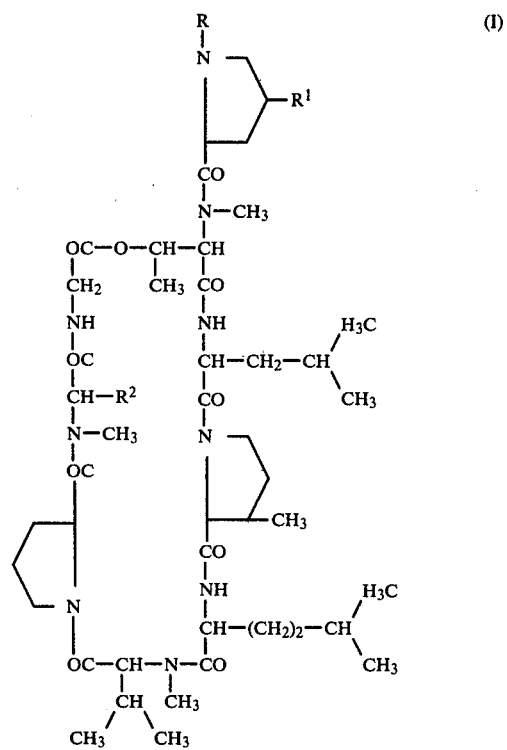

[wherein:
R represents a hydrogen atom, an N-(α-ketobutyryl)-N-methylvalyl group or an N-(α-hydroxybutyryl)-N-methylvalyl group;
$R^1$ represents a methyl group or an ethyl group; and when $R^1$ represents a methyl group, $R^2$ represents an isobutyl group and, when $R^1$ represents an ethyl group, $R^2$ represents a pentyl group] have antibacterial activity which is particularly pronounced against bacteria of the genus Mycobacterium. The compounds in which R represents and N-(α-ketobutyryl)-N-methylvalyl group, named Mycoplanecin B ($R^1$ represents a methyl group) and Mycoplanecin C ($R^1$ represents an ethyl group), may be prepared by cultivation of a microorganism of the genus Actinoplanes, while the compounds where R represents an N-(α-hydroxybutyryl)-N-methylvalyl group or a hydrogen atom can be prepared by reducing the corresponding compound where R represents an N-(α-ketobutyryl)-N-methylvalyl group or by hydrolyzing the corresponding compound where R represents an N-(α-ketobutyryl)-N-methylvalyl or N-(α-hydroxybutyryl)-N-methylvalyl group, respectively.

3 Claims, 6 Drawing Figures

MYCOPLANECIN DERIVATIVES AND THEIR PREPARATION

BACKGROUND TO THE INVENTION

The present invention provides certain new Mycoplanecin derivatives, referred to herein as Mycoplanecin B and Mycoplanecin C, which may be prepared by cultivation of actinomycetes, and compounds prepared by reducing and/or hydrolizing Mycoplanecin B and Mycoplanecin C. The invention also provides processes for preparing these compounds as well as pharmaceutical compositions containing them.

U.S. patent application Ser. No. 041,501 filed May 22, 1979, which issued as U.S. Pat. No. 4,336,249 discloses an antibiotic substance called Mycoplanecin, which may be prepared by cultivating a Mycoplanecin-producing microorganism of the genus Actinoplanes, especially Actinoplanes nov. sp. Strain No. 41042 (FERM 4504). For clarity, this original Mycoplanecin compound is hereafter referred to as "Mycoplanecin A". Subsequently, U.S. patent application Ser. No. 199,238, filed Oct. 21, 1980, disclosed some derivatives of this Mycoplanecin A prepared by reducing the N-($\alpha$-ketobutyryl)-N-methylvalyl group of Mycoplanecin A to an N-($\alpha$-hydroxybutyryl)-N-methylvalyl group or by hydrolizing either Mycoplanecin A or the product obtained by reducing Mycoplanecin A. Mycoplanecin A and its two derivatives have the formula:

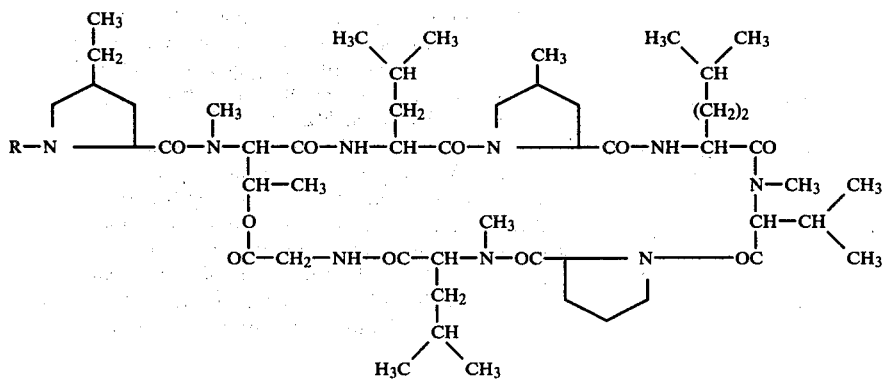

[wherein: R represents a hydrogen atom, an N-($\alpha$-ketobutyryl)-N-methylvalyl group or an N-($\alpha$-hydroxybutyryl)-N-methylvalyl group]. Mycoplanecin A is the compound in which R represents an N-($\alpha$-ketobutyryl)-N-methylvalyl group. Mycoplanecin A and its derivatives have been found to have antibacterial activity, especially against microorganisms of the genus Mycobacterium. We have now discovered that other compounds, structurally related to Mycoplanecin A, can also be produced by microorganisms of the genus Actinoplanes and that these compounds and derivatives thereof also have antibacterial activity.

BRIEF SUMMARY OF INVENTION

The compounds of the present invention have the formula (I):

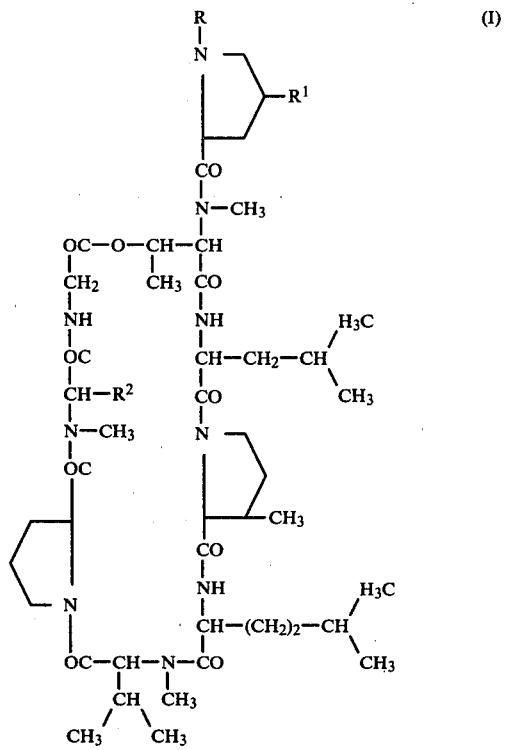

[wherein:
R represents a hydrogen atom, an N-($\alpha$-ketobutyryl)-N-methylvalyl group or an N ($\alpha$-hydroxybutyryl)-N-methylvalyl group;

$R^1$ represents a methyl group or an ethyl group; and when $R^1$ represents a methyl group, $R^2$ represents an isobutyryl group or, when $R^1$ represents an ethyl group, $R^2$ represents a pentyl group].

The invention also provides a process for preparing Mycoplanecin B or Mycoplanecin C [that is those compounds of formula (I) in which R represents an N-($\alpha$-ketobutyryl)-N-methylvalyl group] by cultivating a Mycoplanecin B-producing or Mycoplanecin C-producing microorganism of the genus Actinoplanes in a culture medium therefor and separating the produced Mycoplanecin B or Mycoplanecin C from the resulting culture broth.

The invention further provides a process for preparing compounds of formula (I) wherein R represents an N-(α-hydroxybutyryl)-N-methylvalyl group, that is to say a group of formula:

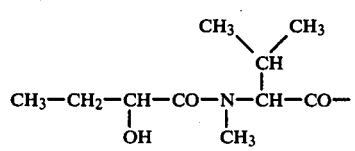

which process comprises reducing a compound of formula (I) in which R represents an N-(α-ketobutyryl)-N-methylvalyl group, that is a group of formula

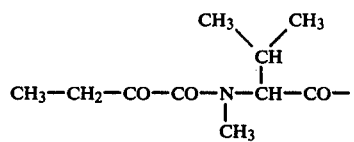

The invention still further provides a process for preparing a compound of formula (I) in which R represents a hydrogen atom, which process comprises hydrolizing a compound of formula (I) in which R represents an N-(α-ketobutyryl)-N-methylvalyl or N-(α-hydroxybutyryl)-N-methylvalyl group.

DETAILED DESCRIPTION OF INVENTION

Figure 1:
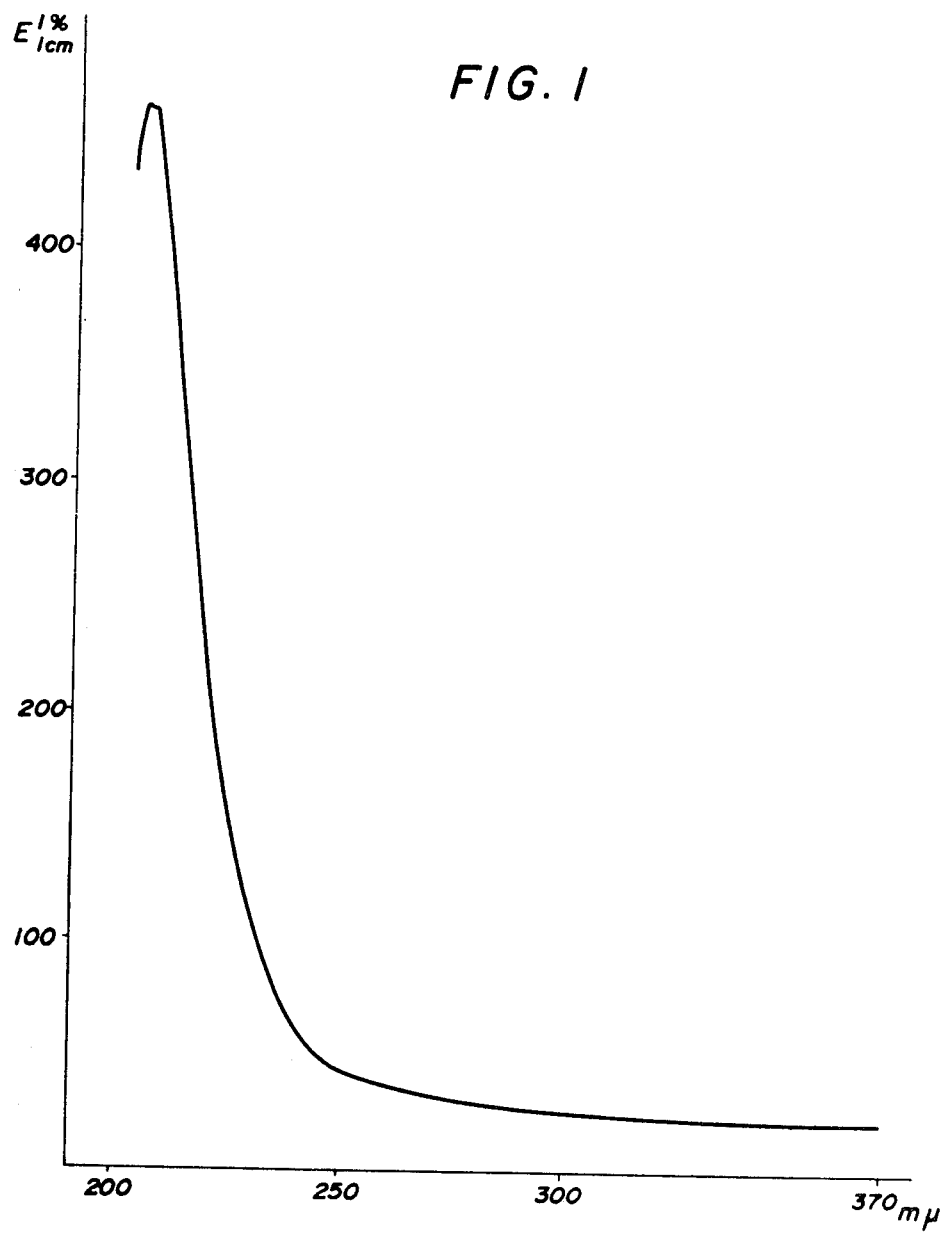

Mycoplanecin B and its derivatives have the formula (II):

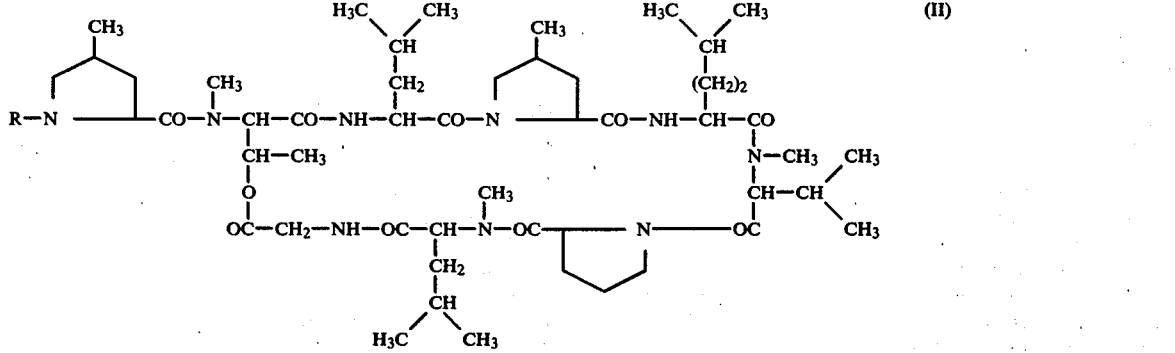

wherein R is as defined above. The compound in which R represents an N-(α-ketobutyryl)-N-methylvalyl group is Mycoplanecin B itself. The compound in which R represents an N-(α-hydroxybutyryl)-N-methylvalyl group is hereafter referred to as compound (IIa) and the compound in which R represents a hydrogen atom is hereafter referred to as compound (IIb).

Mycoplanecin C and its derivatives have the formula (III):

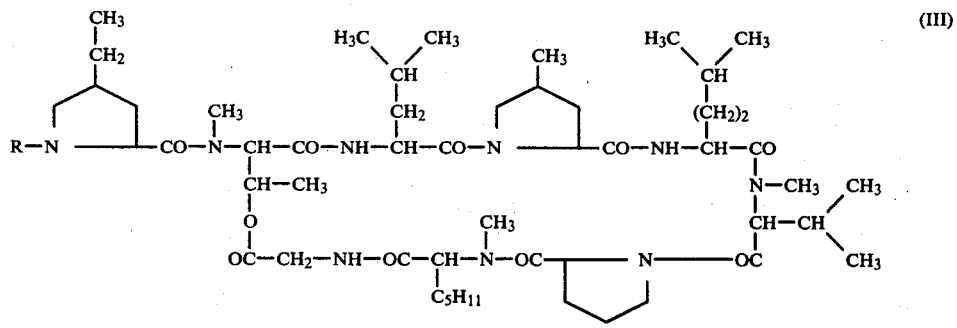

wherein R is as defined above. The compound in which R represents an N-(α-ketobutyryl)-N-methylvalyl group is Mycoplanecin C itself. The compound in which R represents an N-(α-hydroxybutyryl)-N-methylvalyl group is hereafter referred to as compound (IIIa) and the compound in which R represents a hydrogen atom is hereafter referred to as compound (IIIb).

Mycoplanecin B and Mycoplanecin C may be prepared by cultivating suitable strains of the genus Actinoplanes, particularly Actinoplanes nov sp. Strain No. 41042 (which has been deposited under the Accession No. FERM 4504 with The Fermentation Research Institute, Agency of Industrial Science and Technology, Ministry of International Trade and Industry, Japan, and under the Accession No. NRRL 11462 with the Agricultural Research Service Culture Collection, Northern Regional Research Laboratory, Peoria, Ill. U.S.A.). The morphology and physiology of this strain are described in more detail in U.S. patent application Ser. No. 041,501, filed May 22, 1979.

As is well-known, the properties of actinomycetes, including Actinoplanes, strains are not fixed and they readily undergo mutation both through natural causes and as the result of artificial mutation. Although the invention relates to the production of Mycoplanecins B and C especially by the cultivation of Actinoplanes nov. sp. Strain No. 41042, it also includes within its scope the use of mutants of this organism and generally of any Actinoplanes strain which is capable of producing Mycoplanecin B and/or Mycoplanecin C.

The cultivation of the Mycoplanecin B-producing or Mycoplanecin C-producing microorganism, in accordance with the process of the invention, can be performed under conditions conventionally employed for the cultivation of Actinoplanes species. Shaken culture or submerged culture with aeration and agitation in a liquid medium are preferred.

The nutrient medium used for the cultivation can be of a composition such as is conventionally used for the cultivation of actinomycetes. Thus it should contain at least an assimilable carbon source and an assimilable nitrogen source. Examples of suitable assimilable carbon sources include glucose, arabinose, galactose, mannose, sucrose, maltose, dextrin, starch, glycerine, a vegetable fat or oil (such as soybean oil, corn oil or cottonseed oil), an animal fat or oil (such as chicken oil or lard) or fish oil. Examples of suitable assimilable nitrogen sources include soybean meal, peanut meal, cottonseed meal, fish meal, corn steep liquor, oatmeal, skimmed milk, peptone, meat extract, pressed yeast, yeast extract, Casamino acids, sodium nitrate, ammonium nitrate and ammonium sulphate. The culture medium also preferably contains an inorganic salt, for example sodium chloride, potassium chloride, a phosphate, magnesium carbonate, calcium carbonate or calcium chloride. It may also contain minor amounts of various other metal salts, for example, ferrous sulphate, copper sulphate, magnesium sulphate, zinc sulphate or cobalt chloride.

The cultivation is preferably effected in a liquid medium, in which case an anti-foaming agent (for example a silicone oil, a vegetable oil or a surfactant) may be added to the medium. It is also preferred that the cultivation should be effected aerobically, with aeration and agitation. Best results are achieved by effecting the cultivation at a substantially neutral pH value and at a temperature of from 20° to 30° C., more preferably about 28° C.

The titre of Mycoplanecin B or Mycoplanecin C produced in the culture broth as cultivation proceeds can be quantitatively determined by assaying the activity of a sample of the culture broth against a microorganism known to be susceptible, for example *Mycobacterium smegmatis* ATCC 607. The maximum production of Mycoplanecin B and Mycoplanecin C is generally achieved after cultivation for 3–5 days.

Mycoplanecins B and C are present in both the liquid portion and the mycelial portion of the culture broth produced by the process of the invention. In order to recover these compounds from the culture broth on completion of the cultivation, the mycelium and other solids are first removed from the liquid phase, for example by filtration (preferably using diatomaceous earth or a similar material as a filter aid) or by centrifugation. The Mycoplanecin B and Mycoplanecin C which are present in the mycelial portion or the filtrate or the supernatant can then be isolated and purified by conventional techniques suited to its physico-chemical properties.

For example, the Mycoplanecin B or C in the mycelial portion can be extracted by the following procedure: adding a water-miscible solvent (such as methanol, ethanol, isopropanol or acetone) to the mycelial portion; removing the solvent from the extract, e.g. by evaporation under reduced pressure; and then re-extracting the residue with a water-immiscible solvent (such as ethyl acetate, methyl isobutyl ketone or methylene chloride). The Mycoplanecin B or Mycoplanecin C contained in the liquid portion of the culture broth can also be extracted with such a water-immiscible solvent, after which it would normally be combined with the extract from the mycelial portion and concentrated to give a crude extract of Mycoplanecin B or Mycoplanecin C.

Alternatively, the Mycoplanecin B or Mycoplanecin C can be extracted by adding a water-miscible solvent, such as those exemplified above, directly to the culture broth without separating the mycelium from the liquid portion; the resulting extract is filtered and concentrated to remove the solvent and then the residue is re-extracted, as in the procedure described above, with a water-immiscible solvent.

The Mycoplanecin B or Mycoplanecin C thus obtained may be further purified by any of the methods well-known for the purification of compounds having similar physico-chemical properties. However, we prefer to use purification techniques employing an adsorbent or a countercurrent distribution method. Suitable adsorbents include alumina, silica gel, Sephadex (a Trade Mark for a range of polysaccharide-derived organic compounds) or cellulose. We particularly prefer to use a column chromatography separation method employing silica gel as carrier and methanol, ethyl acetate or chloroform or a mixture thereof as eluent. High performance liquid chromatography employing silica gel or another carrier for reversed phase column chromatography is also effective for the production of highly purified Mycoplanecin B or Mycoplanecin C.

The compounds thus obtained show single spots in colouration reactions with sulphuric acid, potassium permanganate or iodine on a silica gel thin layer chromatogram and the physical and chemical properties described hereafter.

Compounds (IIa) and (IIIa) can be prepared by reducing Mycoplanecin B and Mycoplanecin C, respectively. The reducing agent employed may be any such agent capable of reducing the $\alpha$-carbonyl group in the N-($\alpha$-ketobutyryl)-N-methylvalyl side chain to a hydroxy group, provided that the reducing agent and/or the conditions under which the reduction is effected are such that other parts of the Mycoplanecin B or Mycoplanecin C molecule are not affected. Suitable reducing agents include, for example, sodium borohydride, lithium alminium hydride or sodium cyanoborohydride. Alternatively, the Mycoplanecin B or C can be treated with hydrogen gas in the presence of a catalyst (such as palladium-on-charcoal or platinum oxide) in an organic or aqueous-organic solvent. Compounds (IIa) and (IIIa) may also be derived from Mycoplanecin B or Mycoplanecin C, respectively, by treating them with a reducing enzyme produced by a microorganism or animal.

Compound (IIb) can be obtained by the hydrolysis of compound (IIa) or of Mycoplanecin B and similarly compound (IIIb) can be obtained by the hydrolysis of compound (IIIa) or of Mycoplanecin C. The hydrolysis may be effected using organic or inorganic acids in an organic solvent or in an aqueous-organic solvent. Particularly good results are achieved by the hydrolysis of these compounds using hydrochloric acid (preferably of concentration 3–5 N) at room temperature, preferably for a period of from 3 to 5 hours. However, any conventional hydrolysis method capable of removing an acyl group from a nitrogen atom may be employed.

The desired compound (IIa), (IIb), (IIIa) or (IIIb) produced as described above may be isolated from the reaction mixture by conventional methods, particularly by chromatography or recrystallization. The chromatography may be effected using various carriers either separately or in combination and may, if necessary, be carried out repeatedly.

The minimal inhibitory concentrations (MIC) of Mycoplanecins B and C against various microorganisms are shown in the following Table 1, whilst the minimal inhibitory concentrations of compounds (IIa), (IIb), (IIIa) and (IIIb) against *Mycobacterium smegmatis* ATCC 607 are shown in the following Table 2.

TABLE 1

| Test Organism | Medium and conditions | MIC µg/ml Mycoplanecin B | MIC µg/ml Mycoplanecin C |
|---|---|---|---|
| *Mycobacterium smegmatis* ATCC 607 | D | 0.05 | 0.05 |
| *Staphylococcus aureus* 209P JC-1 | H | >400 | >400 |
| *Bacillus subtilis* PCI 219 | H | >400 | >400 |
| *Escherichia coli* NIHJ JC-2 | H | >400 | >400 |
| *Klebsiella pneumoniae* PCI 602 | H | >400 | >400 |
| *Proteus vulgaris* OX19 | H | >400 | >400 |
| *Proteus mirabilis* 1331 | H | >400 | >400 |
| *Pseudomonas aeruginosa* SANK 73860 | H | >400 | >400 |
| *Candida albicans* Yu 1200 | S | >400 | >400 |
| *Aspergillus oryzae* SANK 11262 | S | >400 | >400 |
| *Penicillium chrysogenum* SANK 12768 | S | >400 | >400 |
| *Trichophyton mentagrophytes* SANK 22374 | S | >400 | >400 |
| *Piricularia oryzae* SANK 16975 | S | >400 | >400 |
| *Micrococcus luteus* | H | 0.0125 | 0.0125 |
| *Xanthomonas oryzae* SANK 70274 | W | 12.5 | 12.5 |

TABLE 2

| Compound | Medium and conditions | MIC µg/ml |
|---|---|---|
| (IIa) | D | 0.05 |
| (IIb) | D | 6.25 |
| (IIIa) | D | 0.05 |
| (IIIb) | D | 6.25 |

The media and conditions employed were as follows:
D: 7 days incubation at 37° C. in a 10% w/v albumin-containing Dubos's liquid medium;
H: 24 hours incubation at 37° C. in a heart infusion agar medium;
S: 48 hours incubation at 26° C. in Sabouraud's agar medium;
W: 72 hours incubation at 28° C. in Wakimoto's agar medium.

The production of the compounds of the present invention is further illustrated by the following non-limiting Examples.

EXAMPLE 1

Preparation of Mycoplanecin B

To a 500 ml Sakagushi flask were added 100 ml of a seed culture medium having a pH of 7.0 before sterilization and the following composition (percentages are w/v):

| Glucose | 1% |
|---|---|
| Glycerine | 1% |
| Oatmeal | 0.5% |
| Sucrose | 1% |
| Soybean meal | 2% |
| Casamino acids | 0.5% |
| Pressed yeast | 1% |
| Calcium carbonate | 0.1% |

Into this medium was inoculated a culture of Actinoplanes Strain 41042 (FERM 4504, NRRL 11462), as described in more detail in our U.S. patent application Ser. No. 041,501, filed May 22, 1979. Reciprocal shaking culture was then carried out at 28° C. for 96 hours. A total of 5 Sakagushi flasks were used in a manner identical to that described above and, at the end of the culture period, the resulting culture broth was divided into 25 ml portions.

Each portion of culture broth was inoculated into a 2 liter Erlenmeyer flask (a total of 8 flasks was employed) each containing 500 ml of a culture medium having the same composition as described above. Reciprocal shaking culture was then carried out at 28° C. for 96 hours.

At the end of this time, each Erlenmeyer flask yielded 1.8 liters of a culture liquid; each 1.8 liters was divided into two equal portions and each portion was inoculated into a 600 liter tank, each tank containing 300 liters of a production medium having a pH of 7.2 before sterilization and having the following composition (percentages are w/v):

| Glycerine | 0.5% |
|---|---|
| Sucrose | 2% |
| Soybean meal | 1% |
| Pressed yeast | 1% |
| Corn steep liquor | 0.5% |
| $CoCl_2.6H_2O$ | 0.001% |

Submerged culture was then carried out with aeration at the rate of 300 liters/minute and agitation at 200 revolutions/minute for 96 hours at 28° C.

To each 600 liters of the resulting culture liquid (pH 7.2) were added 30 kg of a Celite 545 (registered Trade Mark) filter aid (a product of Johns Manville Product Corporation, U.S.A.) and the liquid was filtered to separate the liquor (420 liters) from the mycelia-containing filter cake (170 kg). The filtrate was treated with an equal volume of ethyl acetate to recover its Mycoplanecin content, whilst the mycelial cake was extracted twice, each time with 400 liters of a 80% v/v aqueous acetone solution; the acetone from this latter extract (750 liters) was then distilled off under reduced pressure and the residue was extracted with 210 liters of ethyl acetate. The ethyl acetate extracts from the filtrate and from the mycelial cake were combined, and then concentrated to a volume of 2 liters by evaporation under reduced pressure.

The resulting concentrate was then washed, in turn, with 1 liter of a 0.05 N aqueous solution of hydrochloric acid, a 1% w/v aqueous solution of sodium bicarbonate and a saturated aqueous solution of sodium chloride. The washed concentrate was then dried over anhydrous sodium sulphate and then concentrated by evaporation under reduced pressure to give 400 g of an oily substance.

This oily substance was dissolved in 300 ml of benzene and adsorbed on a column containing 900 g of silica gel (a product of Mallinckrodt Co. U.S.A.) which had previously been prepared with benzene. After washing the column with benzene, it was eluted with, in turn, 4 liters of a 3:1 by volume mixture of benzene and ethyl acetate, 4 liters of 2:1 by volume mixture of benzene and ethyl acetate, 4 liters of a 1:1 by volume mixture of benzene and ethyl acetate and finally 4 liters of ethyl acetate alone. The resulting solution was collected in 500 ml fractions, giving a total of 32 fractions.

The desired Mycoplanecin B was mainly eluted in fractions 27 to 30 inclusive, and so these were collected, combined and concentrated by evaporation under reduced pressure to give 5.2 g of an oily substance. 1.5 g of this oily substance was dissolved in 3 ml of acetonitrile and purified by reversed phase column chromatography carried out as follows: the acetonitrile solution was divided into three equal 1 ml portions and each portion was adsorbed on LiChroprep RP-8 (Lobar Column B, manufactured by Merck & Co. Inc.) and the column was then eluted with a 60% v/v aqueous solution of acetonitrile at a flow rate of 10 ml/minute. The desired Mycoplanecin B was eluted between 28 and 36 minutes after adsorption of the sample. Mycoplanecin A, which had also been produced was eluted between 37 and 49 minutes.

Figure 2:
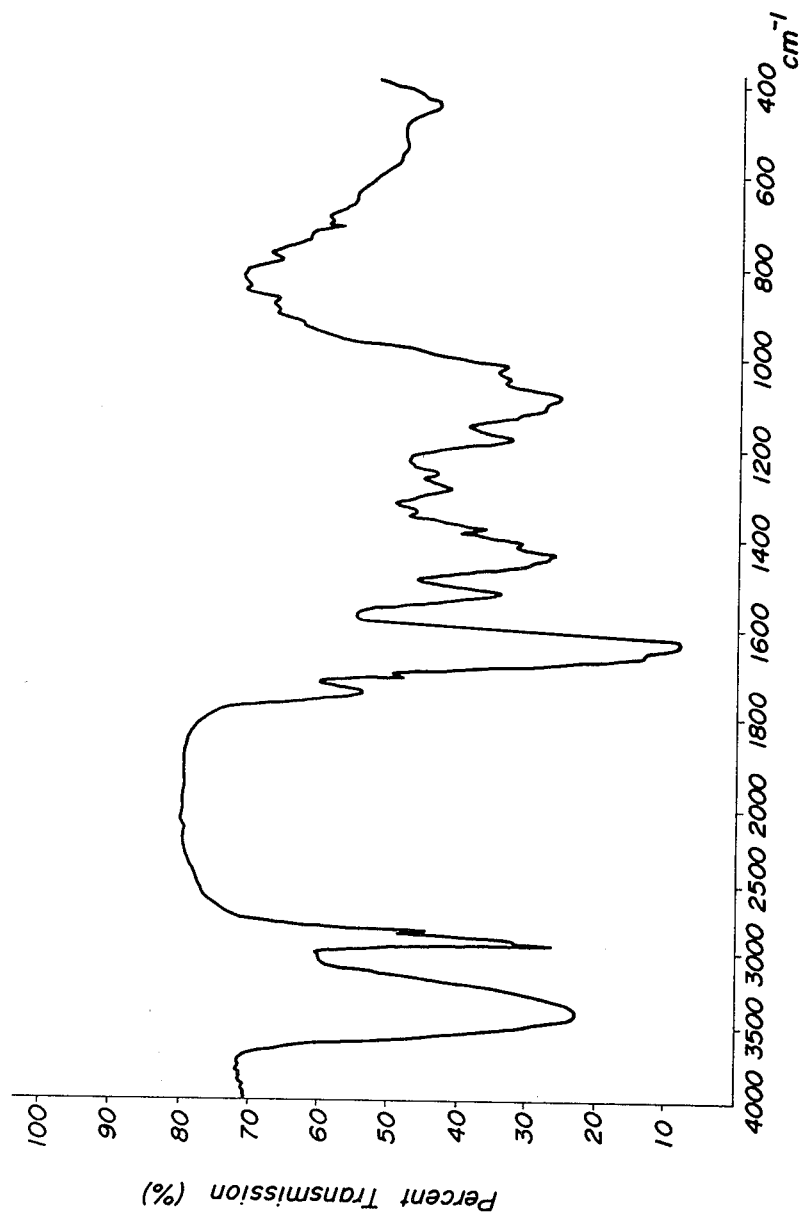
Figure 3:
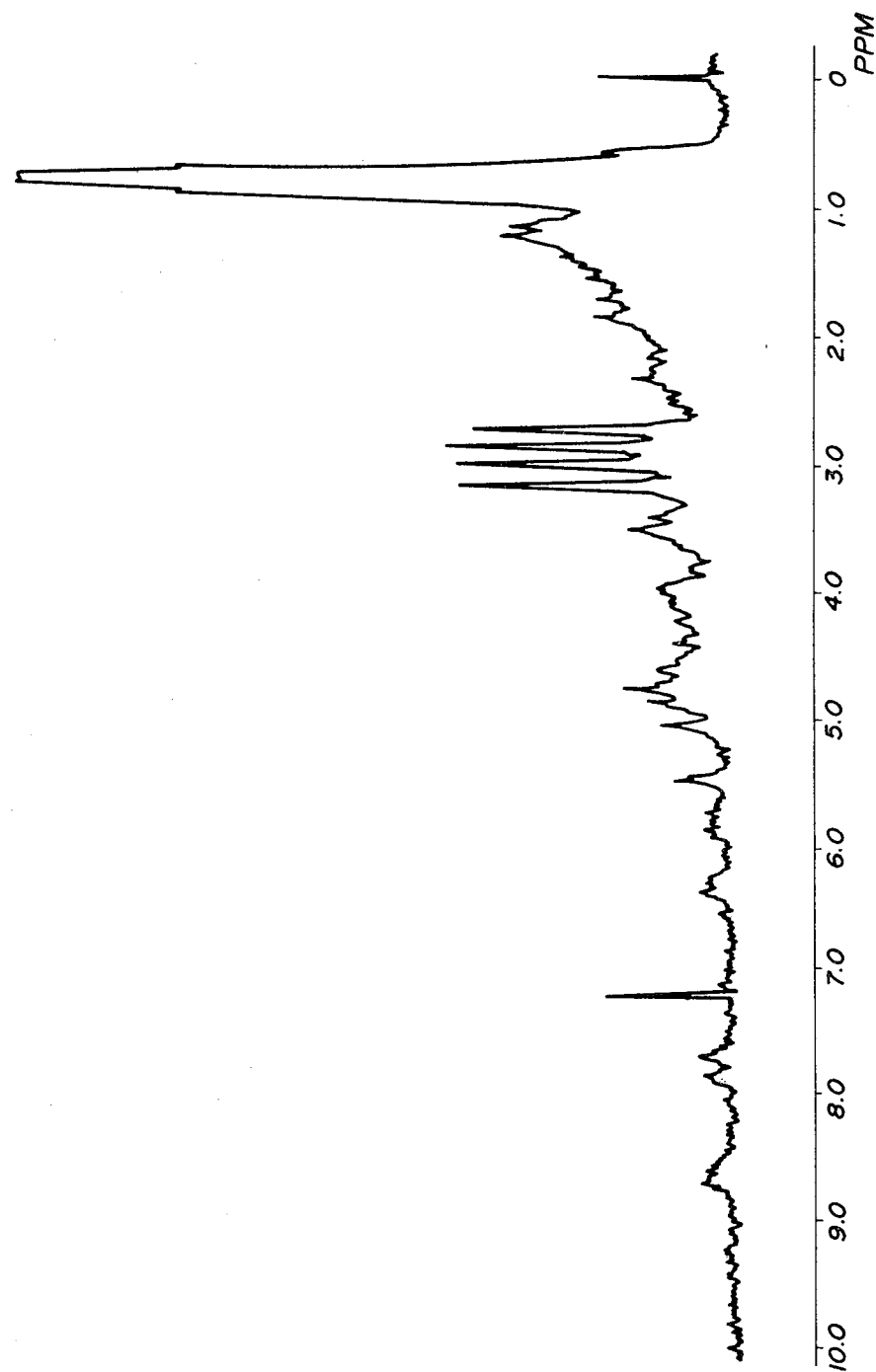

The products from each of the three samples purified by this column chromatography procedure were combined, giving a total of 240 ml of active fractions, from which the acetonitrile was then distilled off under reduced pressure. The resulting residue was extracted with 100 ml of ethyl acetate and this extract was washed with a saturated aqueous solution of sodium chloride and dried over anhydrous sodium sulphate. The solution was then evaporated to dryness, giving 47.7 mg of Mycoplanecin B as a white powder melting at 160°–170° C. and having the following characteristics:

1. Elemental Analysis: Found: C, 61.32%; H, 8.50%; N, 11.86%.
2. Empirical formula: $C_{60}H_{100}N_{10}O_{13}$.
3. Molecular weight: 1168. 4. Specific rotation: $[\alpha]_D^{21} - 72°(c=0.43,$ chloroform).
5. Ultraviolet Absorption Spectrum: At a concentration of 20 μg/ml in a 50% v/v aqueous methanolic solution shows only terminal absorption, as illustrated in FIG. 1 of the accompanying drawings.
6. Infrared Absorption Spectrum: As shown in FIG. 2 of the accompanying drawings, measured in a KBr disc.
7. Nuclear Magnetic Resonance Spectrum: As shown in FIG. 3 of the accompanying drawings, measured in deuterochloroform, using tetramethylsilane as the internal standard.
8. Solubility: Soluble in methanol, ethanol, ethyl acetate, acetone and chloroform. Insoluble in water.
9. Colour reactions: A brown colour develops on treatment with 50% v/v aqueous sulphuric acid. Positive for iodine and potassium permanganate. Negative for ninhydrin and 2,4-dinitrophenylhydrazine.
10. Amino acid analysis: 1 mole each of proline, glycine, leucine, 2-amino-5-methylhexanoic acid, N-methylthreonine and N-methylleucine; and 2 moles each of methylproline and N-methylvaline. Analysis was effected after hydrolysis with a 1:1 by volume mixture of concentrated hydrochloric acid and acetic acis at 105° C. for 20 hours.
11. $R_f$ value (silica gel thin layer chromatography, $F_{254}$, 0.25 mm thick, No. 5714, manufactured by Merck & Co. Inc.):
   0.14 (developed with ethyl acetate)
   0.62 (developed with 95:5 by volume mixture of chloroform and methanol).

EXAMPLE 2

Preparation of Compound (IIa)

To a solution of 100 mg of Mycoplanecin B in 5 ml of methanol were added, with ice-cooling, 5 mg of sodium borohydride, after which the mixture was stirred for 1 hour. At the end of this time, the reaction mixture was concentrated by evaporation under reduced pressure and 20 ml of ethyl acetate were added to the residue. The mixture was then washed twice, each time with 10 ml of a saturated aqueous solution of sodium chloride. The washed mixture was dehydrated over anhydrous sodium sulphate and then concentrated by evaporation to dryness. The residue was dissolved in a small amount of acetonitrile and left to stand at room temperature. There were obtained 75 mg of the desired compound (IIa) in the form of colourless needles melting at 165°–173° C. and having the following characteristics:

1. Elemental Analysis: C, 61.50%; H, 8.70%; N, 11.90%.
2. Empirical formula: $C_{60}H_{102}N_{10}O_{13}$.
3. Molecular weight: 1170.
4. Specific rotation: $[\alpha]_D^{25} - 75.6°$ (c=0.4, chloroform).
5. Ultraviolet Absorption Spectrum: In methanol, only terminal absorption.
6. Infrared Absorption Spectrum (KBr) $\nu_{max}$cm$^{-1}$: 1760, 1670–1640.
7. Solubility: Soluble in methanol, acetone, ethyl acetate, chloroform and benzene. Insoluble in water and hexane.
8. $R_f$ value (silica gel thin layer chromatography, $F_{254}$, 0.25 mm thick, No. 5715, manufactured by Merck & Co. Inc.):
   0.08 (developed with ethyl acetate).

EXAMPLE 3

Preparation of Compound (IIb) 50 mg of compound (IIIa) were dissolved in 1 ml of a 4.5 N methanolic solution of hydrogen chloride, and the resulting solution was stirred for 4 hours at room temperature (25° C.). At the end of this time, the reaction mixture was repeatedly concentrated by evaporation under reduced pressure to remove hydrogen chloride. The resulting residue was dissolved in 10 ml of ethyl acetate and this ethyl acetate solution was washed, in turn, with 5 ml of a 2% w/v aqueous solution of sodium bicarbonate and with a saturated aqueous solution of sodium chloride. The solution was then dried over anhydrous sodium sulphate and concentrated by evaporation under reduced pressure. The concentrated solution was allowed to stand at room temperature, to give 22 mg of the desired compound (IIb) in the form of colourless crystals melting at 140°–150° C. and having the following characteristics:

1. Elemental Analysis: C, 61.45%; H, 8.73%; N, 12.65%.
2. Empirical formula: $C_{50}H_{85}N_9O_{10}$.
3. Molecular weight: 971.
4. Specific rotation $[\alpha]_D^{25} - 56°$ (c=0.5, chloroform)
5. Ultraviolet Absorption Spectrum: In methanol, only terminal absorption.
6. Infrared Absorption Spectrum (KBr) $\nu_{max}$cm$^{-1}$: 1760, 1670–1640.
7. Solubility: Soluble in methanol, acetone, ethyl acetate and chloroform. Insoluble in water, benzene and hexane.
8. $R_f$ value (silica gel thin layer chromatography, $F_{254}$, 0.25 mm thick, No. 5715, manufactured by Merck & Co. Inc.):
   0.18 (developed with a 90:10:1 by volume mixture of chloroform, methanol and ammonium hydroxide).

EXAMPLE 4

Preparation of Mycoplanecin C

To a 500 ml Sakaguchi flask were added 100 ml of a seed culture medium having a pH of 7.0 before sterilization end the following composition (percentages are w/v):

| | |
|---|---|
| Glucose | 1% |
| Glycerine | 1% |
| Oatmeal | 0.5% |
| Sucrose | 1% |
| Soybean meal | 2% |
| Casamino acids | 0.5% |
| Pressed yeast | 1% |
| Calcium carbonate | 0.1% |

Into this medium was inoculated a culture of Actinoplanes Strain 41042 (FERM 4504, NRRL 11462), as described in more detail in our U.S. patent application Ser. No. 041,501, filed May 22, 1979. Reciprocal shaking culture was then carried out at 28° C. for 96 hours. A total of 5 Sakaguchi flasks were used in a manner identical to that described above and, at the end of the culture period, the resulting culture broth was divided into 25 ml portions.

Each portion of culture broth was inoculated into a 2 liter Erlenmeyer flask (a total of 8 flasks was employed) each containing 500 ml of a culture medium having the same composition as described above. Reciprocal shaking culture was then carried out at 28° C. for 96 hours.

At the end of this time, each Erlenmeyer flask yielded 1.8 liters of a culture liquid; each 1.8 liters was divided into two equal portions and each portion was inoculated into a 600 liter tank, each tank containing 300 liters of a production medium having a pH of 7.2 before sterilization and having the following composition (percentages are w/v):

| | |
|---|---|
| Glycerine | 0.5% |
| Sucrose | 2% |
| Soybean meal | 1% |
| Pressed yeast | 1% |
| Corn steep liquor | 0.5% |
| $CoCl_2.6H_2O$ | 0.001%. |

Submerged culture was then carried out with aeration at the rate of 300 liters/minute and agitation at 200 revolutions/minute for 96 hours at 28° C.

To each 600 liters of the resulting culture liquid (pH 7.2) were added 30 kg of a Celite 545 (registered Trade Mark) filter aid (a product of Johns Manville Product Corporation, U.S.A.) and the liquid was filtered to separate the liquor (420 liters) from the mycelia- containing filter cake (170 kg). The filtrate was treated with an equal volume of ethyl acetate to recover its Mycoplanecin content, whilst the mycelial cake was extracted twice, each time with 400 liters of a 80% v/v aqueous acetone solution; the acetone from this latter extract (750 liters) was then distilled off under reduced pressure and the residue was extracted with 210 liters of ethyl acetate. The ethyl acetate extracts from the filtrate and from the mycelial cake were combined, and then concentrated to a volume of 2 liters by evaporation under reduced pressure.

The resulting concentrate was then washed, in turn, with 1 liter of a 0.05 N aqueous solution of hydrochloric acid, a 1% w/v aqueous solution of sodium bicarbonate and a saturated aqueous solution of sodium chloride. The washed concentrate was then dried over anhydrous sodium sulphate and then concentrated by evaporation under reduced pressure to give 400 g of an oily substance.

This oily substance was dissolved in 300 ml of benzene and adsorbed on a column containing 900 g of silica gel (a product of Mallinckrodt Co. U.S.A.) which had previously been prepared with benzene. After washing the column with benzene, it was eluted with, in turn, 4 liters of a 3:1 by volume mixture of benzene and ethyl acetate, 4 liters of a 2:1 by volume mixture of benzene and ethyl acetate, 4 liters of a 1:1 by volume mixture of benzene and ethyl acetate and finally 4 liters of ethyl acetate alone. The resulting solution was collected in 500 ml fractions, giving a total of 32 fractions.

The desired Mycoplanecin C was mainly eluted in fractions 17 to 22 inclusive, and so these were collected, combined and concentrated by evaporation under reduced pressure to give 15.0 g of an oily substance. 5 g of this oily substance was dissolved in 3 ml of acetonitrile and purified by reversed phase column chromatography carried out as follows: the acetonitrile solution was divided into three equal 1 ml portions and each portion was adsorbed on LiChroprep RP-8 (Lobar Column B, manufactured by Merck & Co. Inc.) and the column was then eluted with a 60% v/v aqueous solution of acetonitrile at a flow rate of 10 ml/minute. The desired Mycoplanecin C was eluted between 50 and 70 minutes after adsorption of the sample. Mycoplanecin A, which had also been produced was eluted between 37 and 49 minutes.

Figure 4:
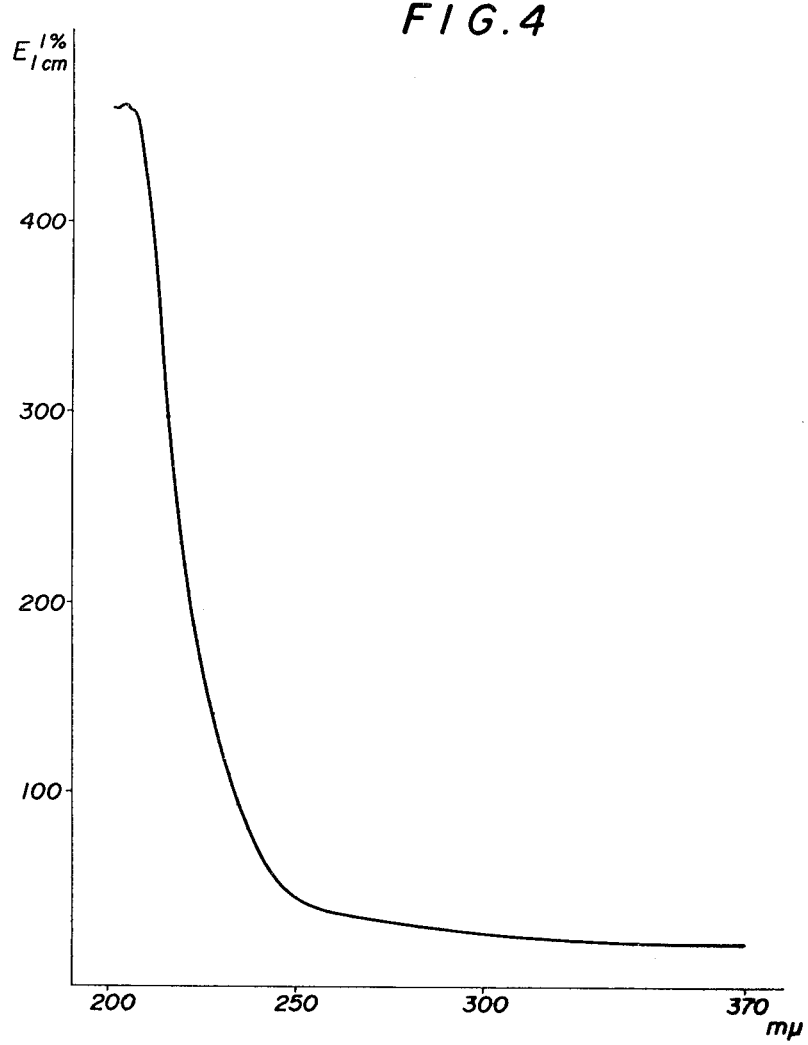
Figure 5:
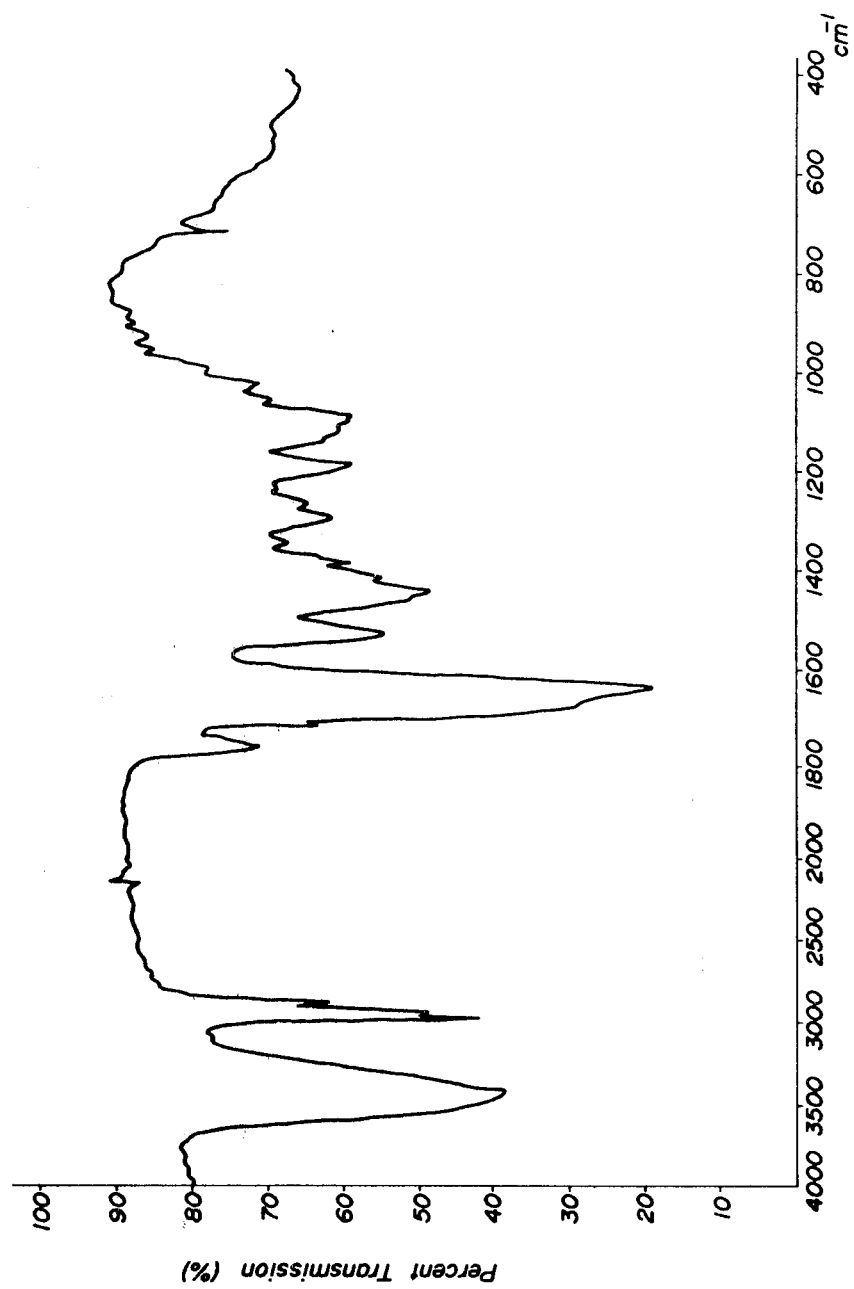
Figure 6:
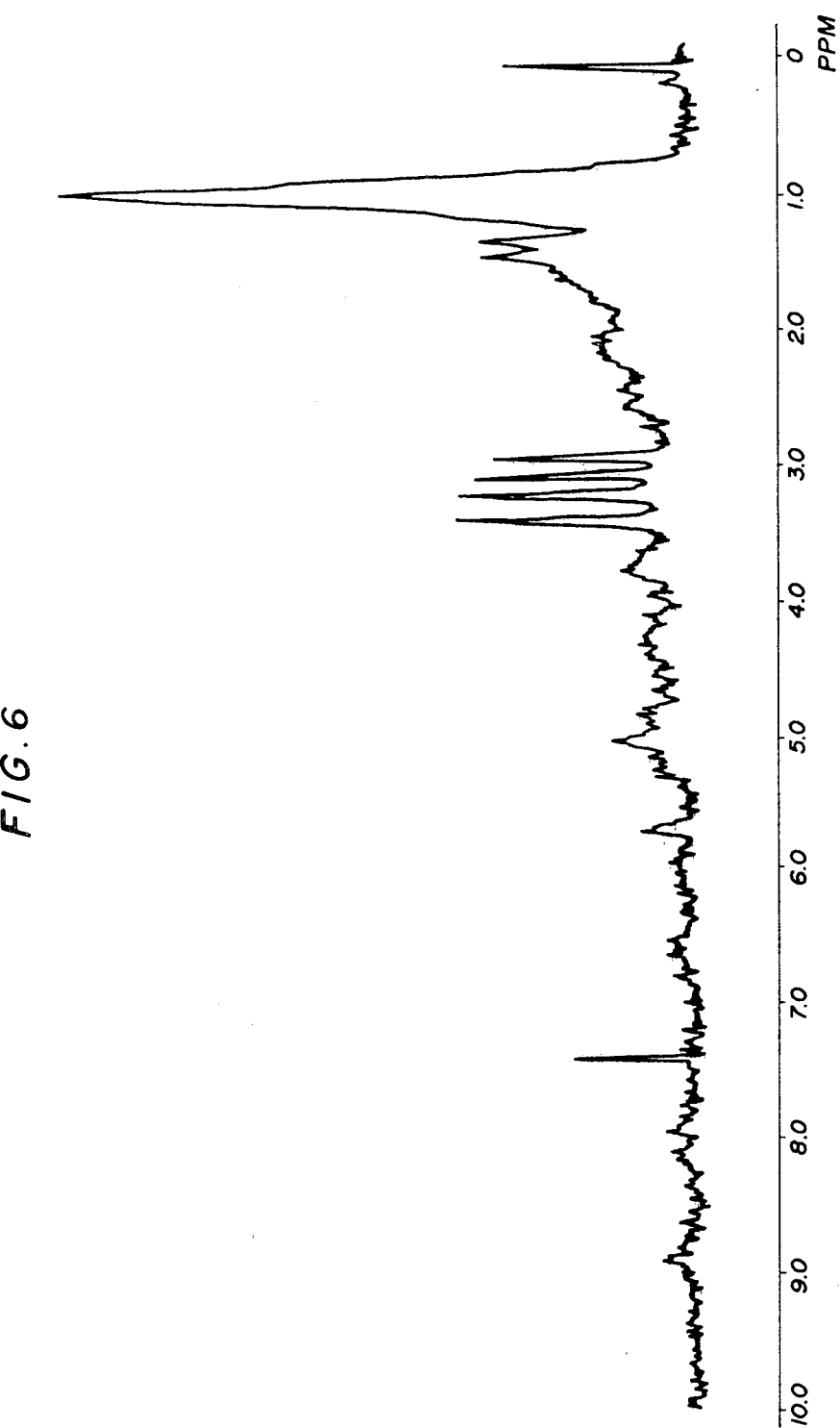

The products from each of the three samples purified by this column chromatography procedure were combined, giving a total of 600 ml of active fractions, from which the acetonitrile was then distilled off under reduced pressure. The resulting residue was extracted with 100 ml of ethyl acetate and this extract was washed with a saturated aqueous solution of sodium chloride and dried over anhydrous sodium sulphate. The solution was then evaporated to dryness, giving 20 mg of Mycoplanecin C as a white powder melting at 159°–165° C. and having the following characteristics:

1. Elemental Analysis: Found: C, 62.04%; H, 8.36%; N, 11.57%.
2. Empirical formula: $C_{62}H_{104}N_{10}O_{13}$.
3. Molecular weight: 1196.
4. Specific rotation: $[\alpha]_D^{21} -70°$ (c=0.2, chloroform).
5. Ultraviolet Absorption Spectrum: At a concentration of 20 μg/ml in a 50% v/v aqueous methanolic solution shows only terminal absorption, as illustrated in FIG. 4 of the accompanying drawings.
6. Infrared Absorption Spectrum: As shown in FIG. 5 of the accompanying drawings, measured in a KBr disc.
7. Nuclear Magnetic Resonance Spectrum: As shown in FIG. 6 of the accompanying drawings, measured in deuterochloroform, using tetramethylsilane as the internal standard.
8. Solubility: Soluble in methanol, ethanol, ethyl acetate, acetone and chloroform. Insoluble in water.
9. Colour reactions: A brown colour develops on treatment with 50% v/v aqueous sulphuric acid. Positive for iodine and potassium permanganate. Negative for ninhydrin and 2,4-dinitrophenylhydrazine.
10. Amino acid analysis: 1 mole each of proline, methylproline, ethylproline, glycine, leucine, 2-amino-5- methylhexanoic acid, N-methylthreonine and an N-methylamino acid having 7 carbon atoms; and 2 moles of N-methylvaline. Analysis was effected after hydrolysis with a 1:1 by volume mixture of concentrated hydrochloric acid and acetic acid at 105° C. for 20 hours.

11. $R_f$ value (silica gel thin layer chromatography, $F_{254}$, 0.25 mm thick, No. 5714, manufactured by Merck & Co. Inc):

0.14 (developed with ethyl acetate)

0.62 (developed with 95:5 by volume mixture of chloroform and methanol.

12. High performance liquid chromatography (Waters Co.): The retention time of the compound was 40.8 minutes when performed under the following conditions:

column, μ Bondapak $C_{18}$ (3.9×30 mm)
solvent, 40% v/v aqueous acetonitrile
flow rate, 1.5 ml/minute
detection, UV 215 mμ.

The retention time of Mycoplanecin A was 29.7 minutes when performed under the same conditions.

EXAMPLE 5

Preparation of Compound (IIIa)

To a solution of 85 mg of Mycoplanecin C in 5 ml of methanol were added, with ice-cooling, 5 mg of sodium borohydride, after which the mixture was stirred for 1 hour. At the end of this time, the reaction mixture was concentrated by evaporation under reduced pressure and 20 ml of ethyl acetate were added to the residue. The mixture was then washed twice, each time with 10 ml of a saturated aqueous solution of sodium chloride. The washed mixture was dehydrated over anhydrous sodium sulphate and then concentrated by evaporation to dryness. The residue was dissolved in a small amount of acetonitrile and left to stand at room temperature. There were obtained 62 mg of the desired compound (IIIa) in the form of colourless needles melting at 163°-168° C. and having the following characteristics:

1. Elemental Analysis: C, 62.15%; H, 8.86%; N, 11.79%.
2. Empirical formula: $C_{62}H_{106}N_{10}O_{13}$.
3. Molecular weight: 1198.
4. Specific rotation: $[\alpha]_D^{25} -73°$ (c=0.2, chloroform).
5. Ultraviolet Absorption Spectrum: In methanol, only terminal absorption.
6. Infrared Absorption Spectrum (KBr) $\nu_{max}$cm$^{-1}$: 1760, 1670-1640.
7. Solubility: Soluble in methanol, acetone, ethyl acetate, chloroform and benzene. Insoluble in water and hexane.
8. $R_f$ value(silica gel thin layer chromatography, $F_{254}$, 0.25 mm thick, No. 5715, manufactured by Merck & Co. Inc.):

0.08 (developed with ethyl acetate).

EXAMPLE 6

Preparation of Compound (IIIb)

40 mg of compound (IIIa) were dissolved in 1 ml of a 4.5 N methanolic solution of hydrogen chloride, and the resulting solution was stirred for 4 hours at room temperature (25° C.). At the end of this time, the reaction mixture was repeatedly concentrated by evaporation under reduced pressure to remove hydrogen chloride. The resulting residue was dissolved in 10 ml of ethyl acetate and this ethyl acetate solution was washed, in turn, with 5 ml of a 2% w/v aqueous solution of sodium bicarbonate and with a saturated aqueous solution of sodium chloride. The solution was then dried over anhydrous sodium sulphate and concentrated by evaporation under reduced pressure. The concentrated solution was allowed to stand at room temperature, to give 15 mg of the desired compound (IIIb) in the form of colourless crystals having the following characteristics:

1. Elemental Analysis: C, 62.64%; H, 8.97%; N, 12.53%.
2. Empirical formula: $C_{52}H_{89}N_9O_{10}$.
3. Molecular weight: 999.
4. Ultraviolet Absorption Spectrum: In methanol, only terminal absorption.
5. Infrared Absorption Spectrum (KBr) $\nu_{max}$cm$^{-1}$: 1760, 1670-1640.
6. Solubility: Soluble in methanol, acetone, ethyl acetate and chloroform. Insoluble in water, benzene and hexane.
7. $R_f$ value (silica gel thin layer chromatography, $F_{254}$, 0.25 mm thick, No. 5715, manufactured by Merck & Co. Inc.):

0.18 (developed with a 90:10:1 by volume mixture of chloroform, methanol and ammonium hydroxide).

We claim:

1. Compounds of formula (I):

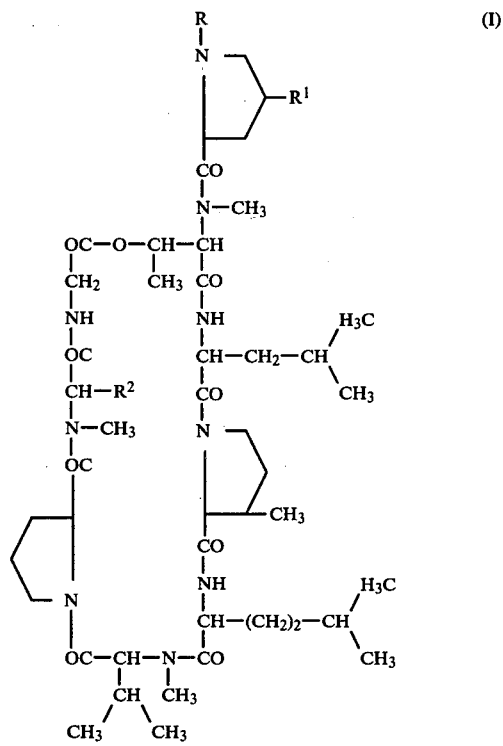

wherein:

R represents a hydrogen atom, an N-(α-ketobutyryl)-N-methylvalyl group or an N-(α-hydroxybutyryl)-N-methylvalyl group;

$R^1$ represents a methyl group or an ethyl group; and when $R^1$ represents a methyl group, $R^2$ represents an isobutyl group, and, when $R^1$ represents an ethyl group, $R^2$ represents a pentyl group.

2. Mycoplanecin B and its derivatives having the formula:

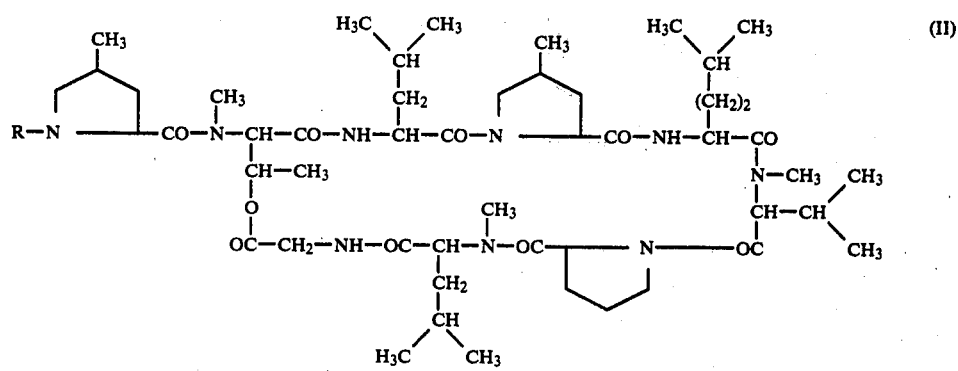
wherein R represents a hydrogen atom, an N-(α-ketobutyryl)-N-methylvalyl group or an N-(α-hydroxybutyryl)-N-methylvalyl group.
3. Mycoplanecin C and its derivatives having the formula:
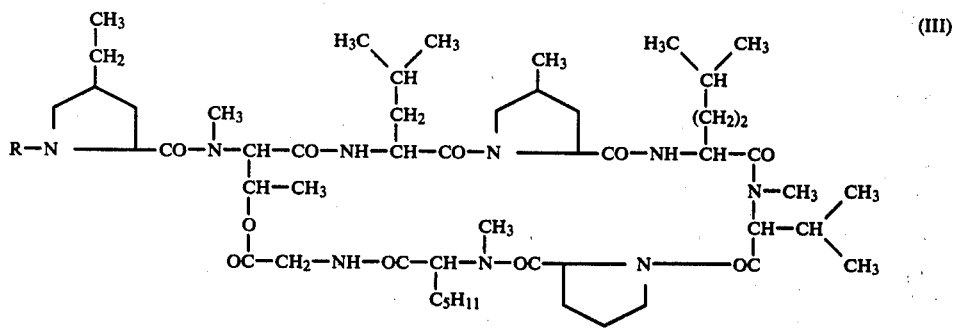
wherein R represents a hydrogen atom, an N-(α-ketobutyryl)-N-methylvalyl group or an N-(α-hydroxybutyryl)-N-methylvalyl group.
* * * * *